(12) United States Patent
Scheumann et al.

(10) Patent No.: US 9,322,766 B2
(45) Date of Patent: Apr. 26, 2016

(54) RAPID TEST METHOD FOR EVALUATING THE DELAMINATION TENDENCY OF GLASS PACKAGING MEANS

(71) Applicant: SCHOTT AG, Mainz (DE)

(72) Inventors: Volker Scheumann, Mainz (DE); Michaela Klause, Woerrstadt (DE); Uwe Rothhaar, Birkenheide (DE)

(73) Assignee: SCHOTT AG, Mainz (DE)

( * ) Notice: Subject to any disclaimer, the term of this patent is extended or adjusted under 35 U.S.C. 154(b) by 176 days.

(21) Appl. No.: 14/354,741

(22) PCT Filed: Oct. 24, 2012

(86) PCT No.: PCT/EP2012/071066
§ 371 (c)(1),
(2) Date: Apr. 28, 2014

(87) PCT Pub. No.: WO2013/060728
PCT Pub. Date: May 2, 2013

(65) Prior Publication Data
US 2014/0240694 A1   Aug. 28, 2014

(30) Foreign Application Priority Data
Oct. 27, 2011   (DE) .......................... 10 2011 085 267

(51) Int. Cl.
*G01N 1/00*   (2006.01)
*G01N 21/01*   (2006.01)
(Continued)

(52) U.S. Cl.
CPC ................ *G01N 21/01* (2013.01); *G01N 21/90* (2013.01); *G01N 21/91* (2013.01)

(58) Field of Classification Search
CPC ......... G01N 1/00; G01N 21/01; G01N 21/90; G01N 21/91
USPC ............................................ 356/36
See application file for complete search history.

(56) References Cited

U.S. PATENT DOCUMENTS

| | | | | |
|---|---|---|---|---|
| 6,114,090 | A * | 9/2000 | Wu ........................ | G02B 1/045 430/281.1 |
| 2013/0327740 | A1* | 12/2013 | Adib ...................... | C03C 3/087 215/379 |
| 2014/0001076 | A1* | 1/2014 | Fadeev .................. | C03C 17/005 206/524.3 |

FOREIGN PATENT DOCUMENTS

DE   102009050714 A1   4/2011

OTHER PUBLICATIONS

Ren Tianfei "Dictionary for Packaging", dated Dec. 31, 1991, p. 311, with English translation, 4 pages.
(Continued)

*Primary Examiner* — Roy M Punnoose
(74) *Attorney, Agent, or Firm* — Ohlandt, Greeley, Ruggiero & Perle, LLP

(57) ABSTRACT

A rapid test method for evaluating the delamination in glass packaging is provided. The method includes exposing the glass packaging means to an atmosphere consisting of steam in order to form a corrosion zone; and subsequently carrying out at least one other step. The other step includes: visualizing the corrosion zone using a light microscope; visualizing the corrosion zone by a staining process with a subsequent inspection process; or removing glass components in ultra-pure water and quantifying the removed glass components. The rapid test method provides a conclusion about whether a glass packaging exhibits a tendency to delaminate or not in a simple and reliable manner and in a relatively short time span.

24 Claims, 8 Drawing Sheets

Figure 1B:
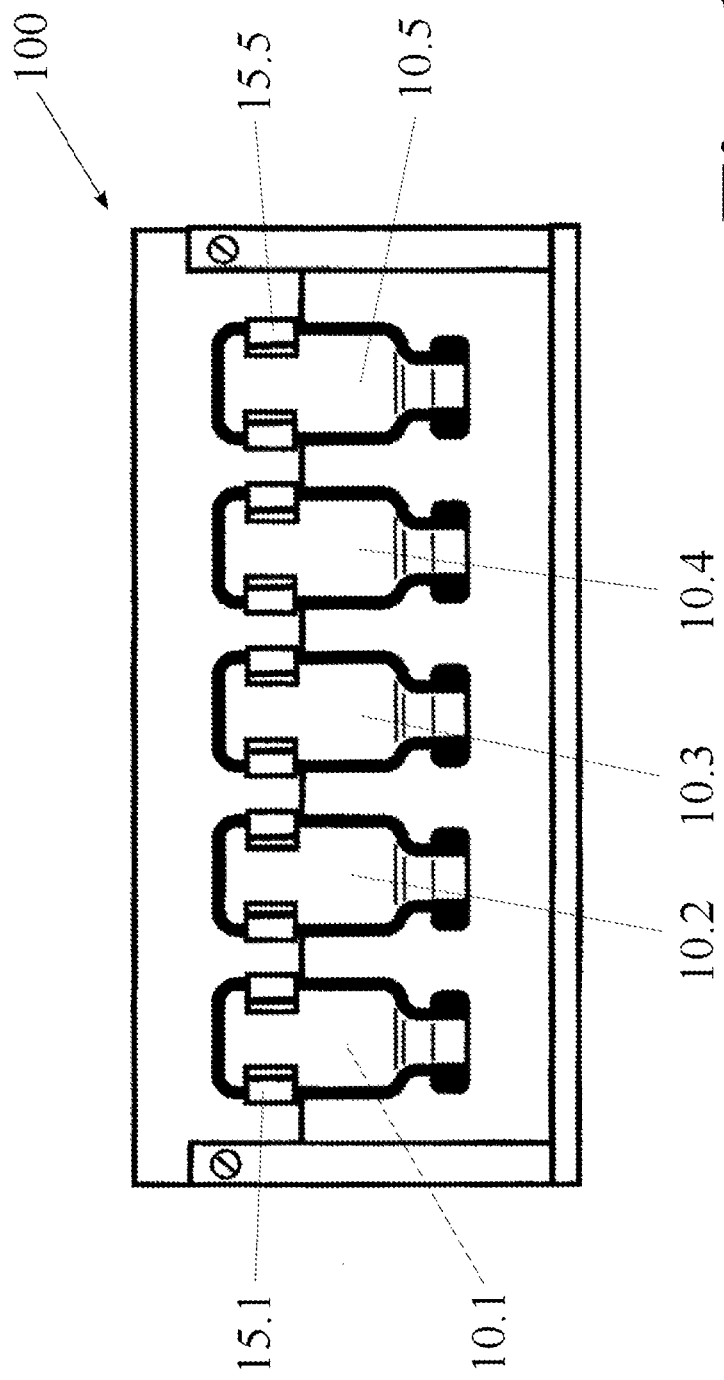

(51) Int. Cl.
  *G01N 21/90* (2006.01)
  *G01N 21/91* (2006.01)

(56) References Cited

OTHER PUBLICATIONS

Iacocca, et al., "Factors Affecting the Chemical Durability of Glass Used in the Pharmaceutical Industry", AAPS PHARMSCITECH, Springer New York LLC, vol. 11, No. 3, Sep. 1, 2010, 10 pp.
Bacon, et al., "Effect of Time and Temperature on Accelerated Chemical Durability Tests Made on Commercial Glass Bottles", Journal of the American Ceramic Society, vol. 23 No. 1, Jan. 1, 1940, pp. 1-9, 9 pp.
Hall, "Delamination in Pharmaceutical Glass Vials", Jan. 1, 2003, pp. 1-19, 19 pp.
Ennis R. D., et al., "Glass Vials for Small Volume Parenterals: Influence of Drug and Manufacturing Processes on Glass Delamination", Pharmaceutical Development and Technology, New York, NY, vol. 6, No. 3, Aug. 1, 2001, 13 pp.
Anonymous, "Detecting Siliceous Flakes in Glass Containers Using Microscopic Techniques", No. 4724, Mar. 11, 2011, 1 pp.
Schmid B., et al.,"Glass Delamination Facts—Prevention-Recommendations", May 1, 2011, p. 1-4, 4 pp.
Wen, Zai-Qing, et al., "Nondestructive Detection of Glass Vial Inner Surface Morphology With Differential Interference Contrast Microscopy", Journal of Pharmaceutical Sciences, American Pharmaceutical Association. vol. 101. No. 4, Apr. 1, 2012, 7 pp.
Collins W. D., et al., "Contamination of Water Samples With Material Dissolved From Glass Containers", Industrial and Engineering Chemistry, vol. 15, No. 1, 1923, 2 pp.
International Search Report dated Apr. 5, 2013 corresponding to PCT/EP2012/071066 with English translation, 7 pp.
International Preliminary Report on Patentability dated Jun. 5, 2014 corresponding to PCT/EP2012/071066, 9 pp.

* cited by examiner

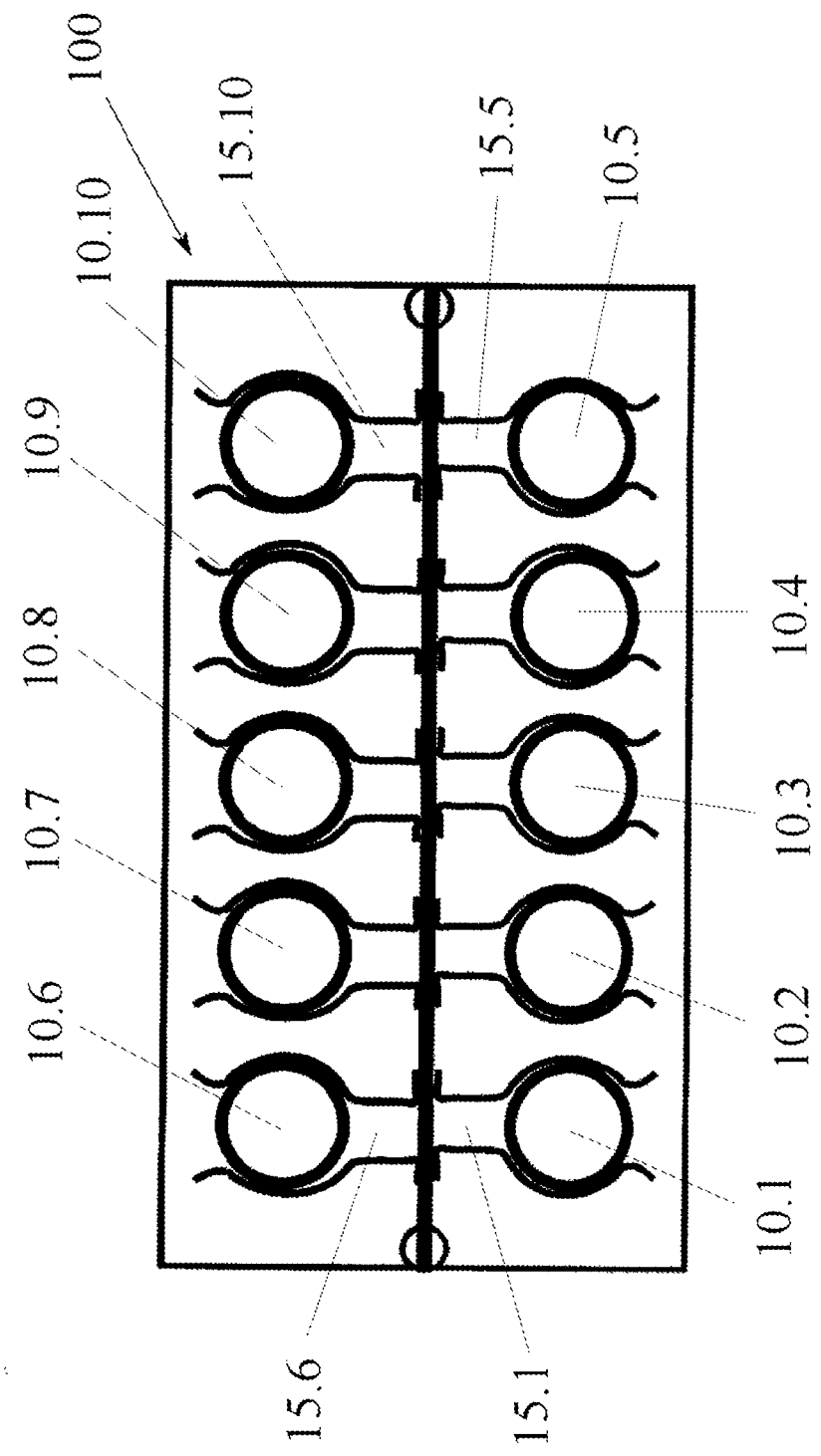

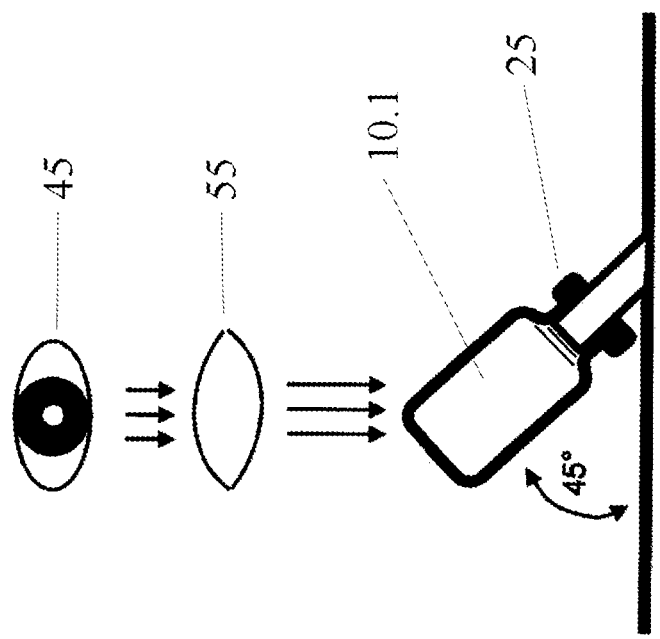

RAPID TEST METHOD FOR EVALUATING THE DELAMINATION TENDENCY OF GLASS PACKAGING MEANS

The invention relates to a rapid test method for evaluating the delamination tendency of glass packaging means, in particular for the pharmaceutical industry.

BACKGROUND OF THE INVENTION

For decades, medicaments have been packaged in vials, ampoules, cartridges or syringes made of glass. The combination of different material properties of glass, in particular the high transparency, the mechanical resistance, the low penetrability and permeability in combination with the high chemical resistance, is critical for maintaining the quality of the medicaments and thus the efficacy thereof.

Despite this general suitability of glass materials, various properties of a medicament (e.g. ionic strength, pH, composition of a buffer present) can, under certain fabrication and storage conditions, lead to chemical reactions even with highly-resistant glasses, such as borosilicate glasses. A possible consequence of such reactions is corrosion processes in which particles in lamellae or leaflet form are formed, which can detach from the glass wall still during the storage period. This behavior of glass is also termed "delamination", owing to the detachment of the particles from the glass wall.

The expression "delamination", which customarily denotes the detachment of layers in compound materials, or the detachment of a corrosion layer on a steel component, was applied to the glass sector for this phenomenon.

The delamination of glass originates from interactions of chemical compounds with the glass surface which are highly complex and are not completely understood. Basically, the process proceeds via 2 mechanisms: the first mechanism is extraction of components from the surface of the glass by a diffusion-controlled ion-exchange process. The second mechanism is the alkaline attack which is also termed hydrolysis or network attack which proceeds in addition to and simultaneously to the first, and effects the dissolution of the glass surface and thereby the release of the components of the glass matrix. Both mechanisms contribute to the delamination of glass; an increase, e.g., in ionic strength, elevation of the pH, increase in the surface to volume ratio, and also thermal processing can amplify the delamination.

The glass composition likewise plays a role in these mechanisms. If glasses have high contents of poorly soluble components, such as, for example, silicon dioxide, aluminum oxide, titanium dioxide and/or oxides of the rare earths, virtually no extraction from the glass matrix is observed, and also no local corrosion occurs. Other components, such as alkali metal oxides and alkaline earth metal oxides, and also the network formation agents boron oxide and phosphorus oxide can in contrast be extracted more readily from the glass matrix.

The extent of delamination depends, as well as on the type and composition of the medicament formulation, and the glass composition, also to a great extent on the selected fabrication process for the glass packaging, such as vials, ampoules, cartridges, syringes and the like. For example, vials formed from a glass tube only exhibit delamination, with formation of the described lamellae, within the wall region that is greatly heated in the reshaping.

In 2009, 2010 and 2011, a great number of medicament batches had to be recalled from the market because of delamination of the glass packaging means that occurred, wherein the most varied products and companies were affected. In addition to the great financial loss and damage to the reputation which such a recall causes, in particular protection of the patient demands avoidance of such damaged packaging material.

As already described, the delamination forms first in the course of storage, and thus cannot be observed by an inspection immediately after charging the medicaments into the corresponding glass packaging means and thereby avoided. In order, nevertheless, to make a prediction on the risk of damaged packaging occurring in a predictable time, for example, accelerated aging tests are used in which the packaged medicament or individual components of the medicament (e.g. placebo solution without active ingredient) are stored, for example at an elevated temperature (30° C. to 60° C.). After an interval of several days, weeks or months, a visual inspection is then made with respect to the characteristic lamellae.

Similar tests are also carried out with buffers usual in pharmacy, such as citrate, phosphate and the like, or with certain test substances, such as solutions containing glutaric acid or glycine.

The known pharmaceutical analyses of glass delamination are therefore concerned principally with the effect of delamination on the medicament quality and are based on studies of the drug present per se, the changes of the properties and efficacy thereof, the purity thereof and the like, i.e. the tests study the changes of the medicament owing to the contact with the inner wall of the glass vessel with the medicament. Such methods are described, for example, in Iacocca, R. G., Toltl, N., et al., Factors Affecting the Chemical Durability of Glass Used in the Pharmaceutical Industry, AAPS PharmSciTech, Aug. 26, 2010; DOI: 10.1208/s12249-010-9506-9; Ennis R D, Pritchard R, et al., Glass vials for small volume parenterals: influence of drug and manufacturing process on glass delamination, Pharm. Dev. and Tech., 2001, 6(3):393-405. Customarily, the tests described in the literature extend over some weeks or a few months.

However, the abovementioned accelerated aging tests have serious disadvantages:

The evaluation proceeds exclusively on the basis of an optical inspection with respect to the presence of lamellae in the medicament. Detachment of the lamellae from the glass wall, however, occurs more or less by chance and can be promoted by mechanical forces, such as by shaking or other external manipulations, for instance. Against this background, only great differences in the delamination tendency may be demonstrated.

In addition, differing compositions of the medicaments have a differing effect on the glass packaging selected, in such a manner that a general statement on glass delamination of the containers cannot be made, but only specific individual cases are ever studied.

Finally, the accelerated aging tests require too much time and are too specific in order to use them in-line during manufacture of the glass packaging means. For this purpose, a test is required which delivers a test result in a relatively short time, that is to say within one day for instance, and thus permits control of the manufacture.

The object of the present invention is therefore to avoid the above-described disadvantages of the prior art and to provide a test method which, in a relatively short time span, and reliably, permits evaluation of the delamination tendency of glass packaging means. The test method should be able to be carried out even before packaging of a medicament into a glass packaging means, in such a manner that the use of damaged or unsuitable packaging material can as far as possible be excluded. The test method should be usable even during manufacture of the glass packaging material or glass packaging means, in order in this manner to be able to perform modifications and/or adaptations of the glass material or the glass packaging means still during the manufacturing process.

DESCRIPTION OF THE INVENTION

According to the invention, the object of the present invention is achieved by a rapid test method for evaluating the delamination tendency in glass packaging means, in particular for the pharmaceutical industry, which has the following steps:
step (1): exposing the glass packaging means to an atmosphere of steam to form a corrosion zone;
and subsequently carrying out a further step selected from step (2a), step (2b) or step (2c), comprising
step (2a): visualizing the corrosion zone using a light microscope;
step (2b): visualizing the corrosion zone by staining and subsequent inspection; or
step (2c): dissolving glass components in ultrapure water and quantifying the dissolved glass components.

The method according to the invention is provided in the form of a rapid delamination test and permits a relatively rapid evaluation of the delamination tendency of glass packaging means, in particular for the pharmaceutical industry.

"Glass packaging means", in the context of the invention, are taken to mean without restriction any packages made of glass. This represents any type of packages which are made of glass and are known from the prior art to a person skilled in the art. There are no restrictions with respect to shape and size of the glass packaging means. Those packages made of glass that are used in the pharmaceutical industry are particularly preferred. Those which may be mentioned by way of example are bottles, in particular vials and phials, ampoules, cartridges, capsules and syringes.

The rapid test method of the invention comprises 2 steps: In step (1) the glass packaging means is exposed to an atmosphere of steam, as a result of which a corrosion zone forms. In step (2) of the rapid test method according to the invention, the corrosion zone in the critical regions is visualized (either step (2a) or step (2b)) or, alternatively, the glass components dissolved out of the packaging means (step (2c)) can be quantified.

Before step (1) is carried out, it is expedient to remove any contaminants present from the glass packaging means, i.e. to clean the glass packaging means before the steam treatment. By this means it can be ensured that the test result is not impaired by contaminants. The cleaning can be carried out, for example, by repeated filling and emptying of the packaging means with water, for example mains water, demineralized water or ultrapure water. Preferably, at least for the last rinse or wash operation, demineralized water or ultrapure water is used, in order to avoid drying residues. The water can be at room temperature, but it can also be preheated to elevated temperature, for example above 50° C. Subsequently thereto, the glass packaging means is dried. The drying is preferably carried out by purging or blowing dry with an inert gas, e.g. nitrogen or purified, oil-free compressed air. Other cleaning methods are likewise possible. However, these should not change the consistency of the glass material, in such a manner that the test result is not falsified thereby.

In step (1) of the rapid test method according to the invention, corrosion of the glass material due to hot steam can take place. The regions on the glass wall of the packaging means which have an increased tendency to delamination have a lower chemical resistance, i.e. a corrosive attack proceeds more rapidly here. These regions are also termed the "critical regions". These are different according to the glass packaging means. In vials or phials, in particular the wall/base transition region is a critical region. The differences in the chemical resistance could be a consequence of the local temperature action in the forming of glass packaging means from tubes.

In the rapid test method of the present invention, therefore the empty (and unsealed) glass packaging means are firstly exposed to an atmosphere of hot steam. The device in which the glass packaging means are exposed to steam is according to the invention likewise not particularly restricted. Preferably, the method step (1), however, is carried out in an autoclave. In this case it is a conventional gas-tight sealable pressure container of any desired size which is usually used for thermal treatment of substances in the overpressure range. In the present case, the autoclave such as for sterilizing medical instruments is used, where the air in the autoclave is displaced by steam. This procedure in step (1), which is also termed "autoclaving" in the context of the present invention, is carried out according to the invention preferably for several minutes to several hours, preferably at least 30 minutes, preferably 1 to 8 hours, still more preferably 3 to 6 hours. The temperature is above 100° C. and is preferably in the range from above 100 to 180° C., preferably 110 to 150° C. When an autoclave is used, in step (1) a temperature-dependent overpressure is established. Step (1), however, can also be carried out at atmospheric pressure.

In the glass packaging means under study, the steam effects a corrosive attack on the glass wall by a combination of leaching and hydrolysis. Consequently, in the near-surface region of the glass, a corrosion zone forms which is altered compared with the base glass with respect to composition and morphology and structure. This layer is particularly strongly expressed in the critical regions.

The corrosion layer generated in step (1) mostly has a thickness of less than 1 μm and is therefore unidentifiable with the naked eye. Therefore, evaluation must proceed by other methods. This proceeds in step (2a) using a light microscope, and in step (2b) by staining and subsequent optical inspection. After step (1) has been carried out, it is again expedient to subject the glass packaging means to a cleaning as already described above. For example, rinsing or washing with mains water, demineralized water or ultrapure water can proceed.

Preferably, for the last rinse or wash process, again demineralized water or ultrapure water is used in order to avoid drying residues. The water can be at room temperature, but can also be preheated to elevated temperature, for example above 50° C. In the subsequent blowing dry, for example using inert gas, such as nitrogen, the cleaned glass packaging means are dried in order to exclude adverse effects on the test owing to contaminants.

If the dissolved glass components according to step (2c) are to be quantified, the cleaning using water should be omitted.

In the second method step, i.e. either in step (2a), (2b) or (2c), the corrosion layer formed in the glass in step (1) is evaluated. This second method step is described in detail hereinafter:

Step (2a):
Visualization Using a Light Microscope

Visualization is carried out according to the invention using a light microscope. Particular preference is given to using a stereomicroscope. This is a special light microscope in which a separate beam path is provided for both eyes, in such a manner that both eyes see the object under investigation from a different angle and a "stereo effect" is produced in the form of a spatial visual impression. Using a light microscope, and preferably grazing illumination, the manifestation of interference colors is used as an evaluation base.

The refractive index of the corrosion zone differs from that of the base glass on account of the altered composition and structure. In the case of suitable illumination, some of the light is reflected at the interface to the glass and interferes with the light which is reflected at the surface of the layer. This effect tends to be more pronounced, the more strongly the corrosion layer is pronounced, i.e. the more clearly perceivable the interference colors are.

Step (2b):
Visualization by Staining and Subsequent Inspection

The visualization method described under step (2a) has the disadvantage that to carry it out an expensive microscope is required. Visualization by staining, in contrast, proceeds without a complex device. In addition, stains for staining glass are inexpensive and readily obtainable.

The corrosion zone has a different composition, and, primarily, a "more open" structure than the base glass. Frequently, these zones are rough or even porous. These differences can therefore be made visible by suitable stains. This can be performed, for example, by filling the glass packaging means (after step (1) of the rapid test method has been carried out) with a solution of methylene blue in a solvent such as, for example, water or alcohol, as a result of which a blue staining of the critical regions results.

The evaluation can then proceed via a visual inspection. Expediently, the glass packaging means filled with methylene blue solution are allowed to stand at room temperature for several minutes to several hours, in order to permit a reaction of the corroded regions with the dye. The blue staining is preferably examined with reference to the glass packaging means when it is again empty.

Depending on the manifestation of the blue staining, a greater or lesser or clearly pronounced corrosion zone can be deduced. The stronger is the blue staining and the thicker the corrosion zone, the greater is the tendency of the glass under test to delamination.

Step (2c):
Quantification of the Dissolved Glass Components

In contrast to the methods described under step (2a) and (2b), this is a quantitative determination.

During the formation of the corrosion zone in method step (1), glass components, such as sodium, boron or silicon, are dissolved out of the glass composite and deposited in what is termed an aqueous gel layer on the surface. In order to quantify these dissolved glass components, the glass packaging means, after step (1) has been carried out, are filled with ultrapure water and stored at elevated temperature, preferably above room temperature, in particular above 50° C. The time period for this is preferably some hours. As a rule of thumb for the storage time, 5 to 20 hours, preferably 10 to 20 hours, can be cited.

Alternatively to the storage, the glass packaging means filled with ultrapure water can also be subjected to an autoclaving at temperatures between 80° C. and 150° C., preferably between 100° C. and 130° C., particularly preferably at 121° C. The autoclaving preferably proceeds for a period of 2 hours. Other time periods are possible and depend on the size and shape of the packaging means under test and the glass composition used. Preference is given to time periods from 0.5 to 8 hours.

As a result of this procedure, the gel layer dissolves and the amount or concentration of the dissolved glass components can be determined using familiar methods in trace analysis, e.g. ICP-OES (inductively coupled plasma optical emission spectrometry) or ICP-MS (inductively coupled plasma mass spectrometry) or FAAS (flame atomic absorption spectroscopy). The larger is the amount of dissolved glass elements, the more pronounced is the corrosion from step (1) and the more pronounced is the corrosion, the stronger is the tendency to delamination.

The rapid test method of the invention is distinguished by numerous advantages:

For instance, the method of the invention does not have the abovementioned disadvantages of the prior art. The evaluation of delamination does not proceed on the basis of various medicament formulations charged into the containers, for example based on an optical inspection with respect to the presence of lamellae in the medicament. Rather, the glass that is already present in the form of the finished package is tested directly. Therefore, the tendency of the glass container to delamination is examined and evaluated independently of a medicament that is present. In contrast to the accelerated aging tests known from the prior art, the rapid test method according to the invention requires markedly less time, a result, depending on the choice of the investigation method used is available as soon as within one working shift, but at least within about one day.

The method can be used in-line in the manufacture of the glass packaging means. Therefore, control of manufacturing can also proceed using the rapid test method.

The method according to the invention consists of 2 steps, wherein a selection can be made between three variants in method step (2). Step (2a), step (2b) and step (2c) could also be combined with one another for additional safeguarding of the result obtained. For example, after step (1) has been carried out, step (2a) and step (2b) could be combined, i.e. carried out one after the other, or step (2a) and step (2c) could be combined with one another. However, it is generally sufficient if, after step (1), only one of steps (2a), (2b) or (2c) is carried out.

The method according to the invention is a reliable and easily usable test which permits in a relatively short time the user to have an estimate as to what extent the studied glass containers have a delamination tendency.

Hereinafter, the present invention will be described with reference to an exemplary embodiment which is intended to illustrate the teaching according to the invention, but not to restrict it.

Exemplary Embodiment

Step (1) of the Rapid Test Method According to the Invention

Sample Preparation:

As glass packaging means, vials are used. In order to exclude variations in the individual vials, in this exemplary embodiment in each case 10 vials produced from borosilicate glass tube, type Fiolax®, 2 ml format, are subjected simultaneously to the test. At the start, the vials are inscribed on the outside using a suitable tool such as, e.g., an engraving pen. The vials are then cleaned using mains water at 60° C.

For this purpose the vials are each filled 3 times with the mains water and emptied again. To avoid drying residues, a rinse process with demineralized water then follows. Also, for this purpose, the vials are each filled 3 times and emptied again. The cleaning procedure ends with purging with nitrogen.

Superheated Steam Treatment:

The cleaned vials are then subjected to a superheated steam treatment. For this purpose, they are placed into a sample holder, preferably clamped overhead and placed into a standard autoclave. In FIGS. 1A and 1B the sample receiver 100 for the autoclaving is shown in a schematic simplified view. FIG. 1A shows a plan view of a sample receiver 100 and FIG. 1B shows a side view of FIG. 1A. The vials 10.1, 10.2, ... to 10.10, each of which are fixed with the opening downwards in the sample holders 15.1, 15.2, . . . to 15.10, are the glass packaging means under test. The clamped-in vials 10.1, 10.2, . . . to 10.10 are subjected to an autoclaving, i.e. they are subjected to superheated steam.

The autoclaving is carried out for a period of 4 h at a temperature of 121° C. Other time periods and temperatures are possible and depend on the size and shape of the packaging means under test and the glass composition used.

Owing to the heating-up and cooling-down phases, this gives a total time of approximately 7 h for step (1). After the cooling down, the vials are withdrawn and again rinsed 3 times with demineralized water. After the blowing dry with nitrogen, step (1) can be evaluated in a downstream method step, i.e. either step (2a), (2b) or (2c). There is no rinsing with demineralized water for the alternative method step (2c).

Step (2a) of the Rapid Test Method According to the Invention

Visualization Using a Light Microscope (Stereomicroscope)

For the assessment, in each case one vial is inserted into a suitable sample holder. This is shown schematically and in a simplified manner in FIG. 2A. The vial 10.1 is clamped into a sample holder 25, wherein the angle of inclination is 45° to the horizontal. Then, the clamped vial 10.1 can be assessed visually, shown schematically by the eye 45 in FIG. 2A, by a light microscope, in this exemplary embodiment, a stereomicroscope, illustrated by the lens 55. In the exemplary embodiment shown, the interference colors were characterized by means of a stereomicroscope with 16× enlargement and grazing illumination. Typically, the interference colors are observed, in particular, in the transition region from the base to the wall of the vial 10.1.

Figure 2B:
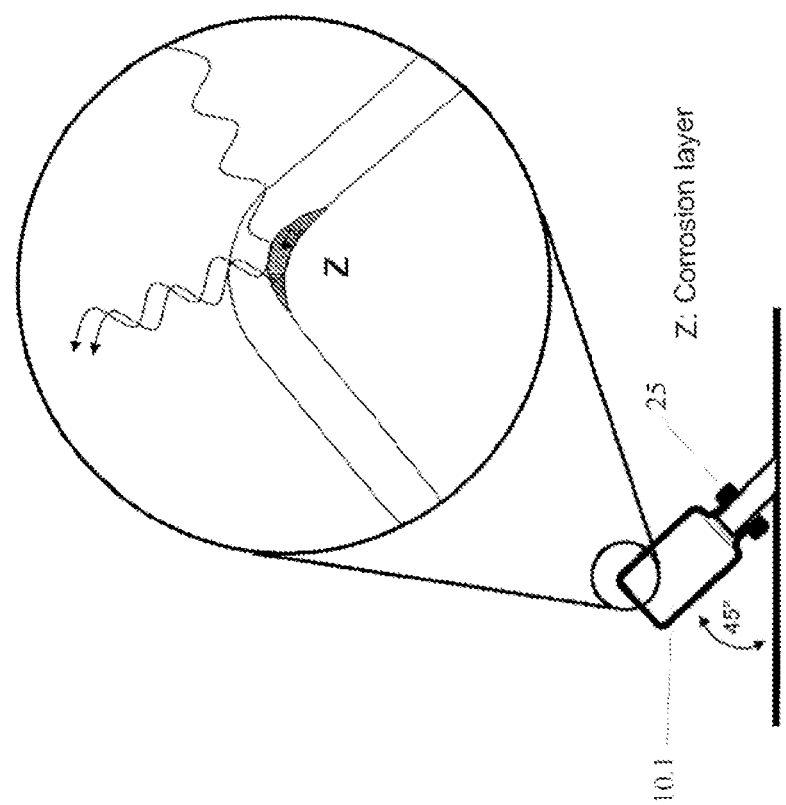

Strong coloring is evaluated as a delamination tendency. The position of the regions in which interferences are observed can vary from vial to vial. In FIG. 2B, the critical region in the form of the transition region between wall and base of the vial 10.1 is shown enlarged in the circle. The corrosion zone Z which is formed, owing to an altered refractive index compared with the base glass, has the effect that some of the light is reflected at the interface to the glass and interferes with the light which is reflected at the surface of the layer. The distinctness of interference colors as a trend increases with the thickness of the corrosion layer. If the thickness of the corrosion layer markedly exceeds the wavelength of the light, in contrast, the effect would decrease again.

Figure 3:
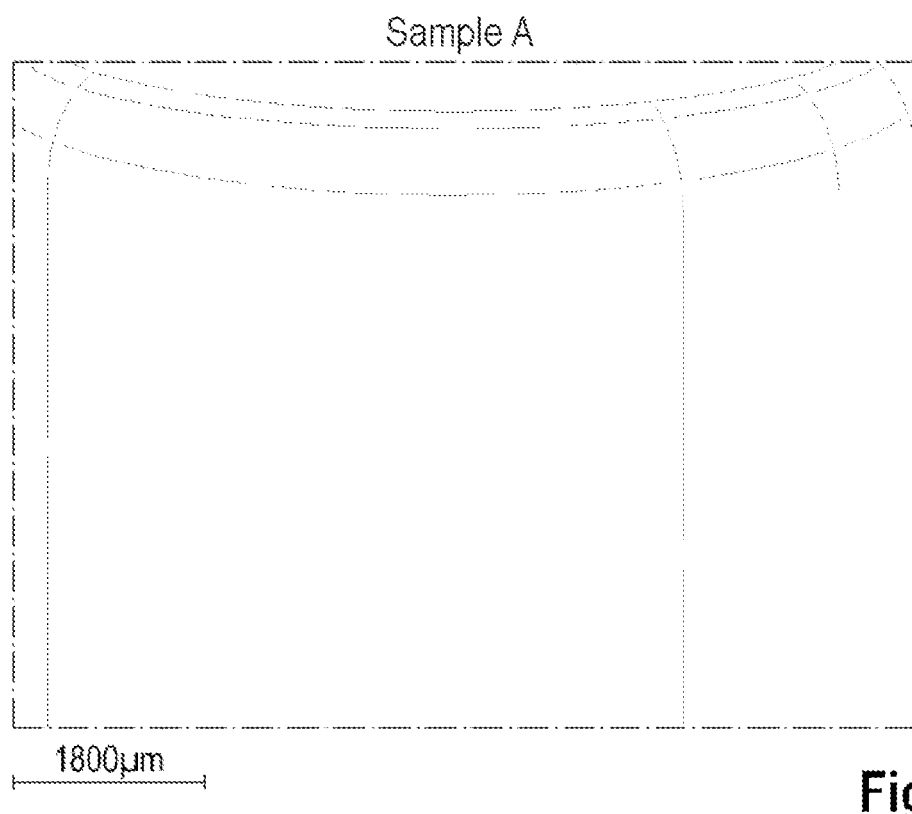
Figure 4:
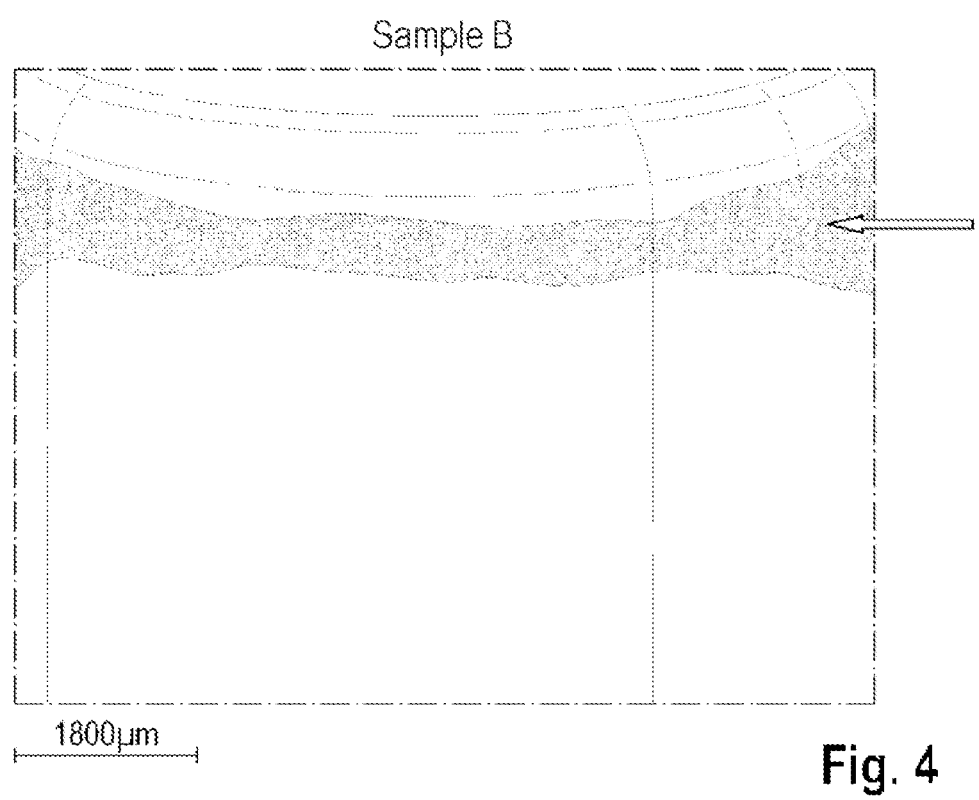

In FIGS. 3 and 4, two stereomicrographs of two different vials (vials 1 and 2) after autoclaving in accordance with method step (1) are shown. FIG. 3 shows vial 1 (sample A) in which, in the wall/base transition region, only slightly pronounced interference colors may be observed. The delamination tendency is therefore to be graded as low for vial 1. In contrast thereto, the interference colors in vial 2 (sample 8) in FIG. 4 are clearly visible in the wall/base transition region. The arrow in FIG. 4 designates the position in the vial 2 where strong interference colors may be seen. This vial 2 is therefore markedly more susceptible to delamination than vial 1.

Step (2b) of the Rapid Test Method According to the Invention

Visualization by Staining

Vials are charged with a methylene blue solution (weight ratio methylene blue/water=1/1000) after the autoclaving, and stored at room temperature (RT) for 12 hours. In accordance with the name of the stain, regions which were changed during the autoclaving are stained blue close to the surface. After the vials are rinsed out with demineralized water (3×), the vials are inspected in the light of a cold-light lamp. Regions which have a delamination tendency are recognizable by a marked blue staining. Vials having a low delamination tendency remain visually inconspicuous in the inspection, i.e. do not show pronounced blue staining.

Figure 5:
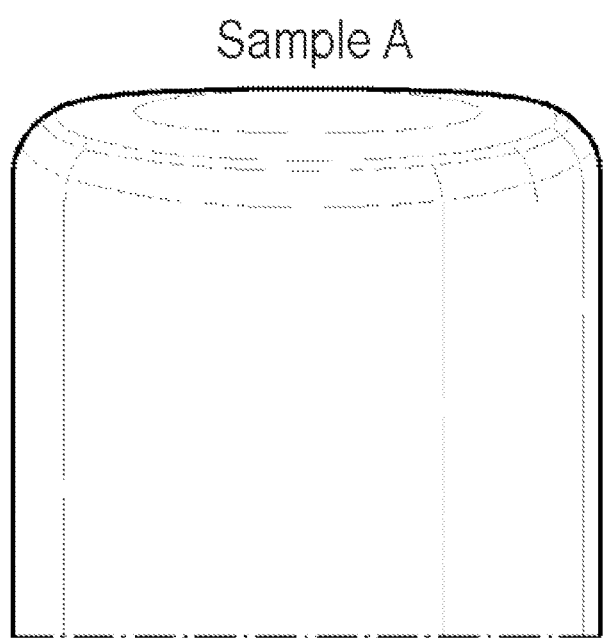
Figure 6:
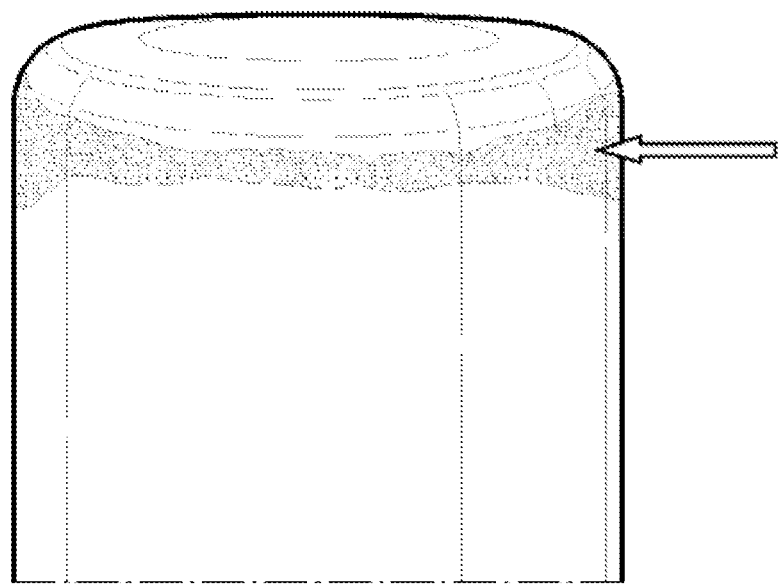

In FIGS. 5 and 6, pictures of two different vials (vials 3 and 4) are shown, as they appear after autoclaving and staining with methylene blue.

Vial 3 (sample A) in FIG. 5 shows no blue staining in the wall/base transition region and is therefore a vial which does not have a delamination tendency. Vial 4, which is shown in FIG. 6, shows marked blue staining in the wall/base transition region after autoclaving and staining using a methylene blue solution, and so vial 4 has a delamination tendency. The arrow in FIG. 6 designates the position in vial 4 where strong blue staining may be observed.

Step (2c) of the Rapid Test Method According to the Invention

Quantification of the Dissolved Glass Elements

After autoclaving, the 10 vials (2 ml format) are not rinsed as previously after carrying out step (1), but, after they are removed from the autoclave, are filled with 1 ml of ultrapure water (R>18.2 MΩ). The amount of water is such that the fill level should be above the critical regions, i.e. the wall/base transition region (reaction zone is wetted with water). The filled vials are then stored for 17 hours at 60° C. Finally, the contents of the vials are withdrawn, for example using a pipette, combined and examined with respect to dissolved glass elements. The silicon is determined in this case by means of ICP-OES, while contents of Na, Al and B are determined by means of ICP-MS. High contents of glass elements indicate a high delamination tendency. Relatively low contents are evidence of a lower susceptibility. In the following table 1, typical values are summarized for the concentration of the glass elements in solution.

TABLE 1

Comparison of the concentration of glass elements

| | Glass element | | | |
|---|---|---|---|---|
| | B [mg/l] | Na [mg/l] | Al [mg/l] | Si [mg/l] |
| Sample C Vial with low delamination tendency | 0.39 | 1.1 | 0.02 | 1.0 |
| Sample D Vial with high delamination tendency | 2.2 | 3.4 | 0.12 | 4.0 |

It can clearly be seen that in the sample having a delamination tendency the values of all elements analyzed are significantly higher by severalfold than the values of the sample that does not have delamination tendency.

The present invention therefore provides for the first time a rapid test method which, in a simple manner, reliably, and in a relatively short time, provides information on whether a glass packaging means has a delamination tendency or not.

The invention claimed is:

1. A rapid test method for evaluating the delamination tendency of glass packaging, comprising the steps of:
exposing empty glass packaging to an atmosphere of steam to form a corrosion zone; and
subsequently carrying out a further step selected from the group consisting of: visualizing the corrosion zone using a light microscope; visualizing the corrosion zone by staining and subsequent inspection; and dissolving glass components in ultrapure water and quantifying the dissolved glass components.

2. The rapid test method as claimed in claim 1, wherein the step of exposing the empty glass packaging to the atmosphere of steam is carried out in an autoclave, wherein the empty glass packaging is exposed to steam for at least 30 minutes.

3. The rapid test method as claimed in claim 2, wherein the empty glass packaging is exposed to steam for 1 to 8 hours.

4. The rapid test method as claimed in claim 1, wherein the step of exposing the empty glass packaging to the atmosphere of steam is carried out at a temperature in a range of from above 100 degrees Celsius to 180 degrees Celsius.

5. The rapid test method as claimed in claim 1, wherein the further step comprises visualizing the corrosion zone using a light microscope, and wherein the light microscope comprises a stereomicroscope or a stereomicroscope having grazing illumination.

6. The rapid test method as claimed in claim 1, wherein the further step comprises visualizing the corrosion zone by staining and subsequent inspection, and wherein the staining is performed using methylene blue, methylene blue in water, or methylene blue alcohol.

7. The rapid test method as claimed in claim 1, wherein the further step comprises visualizing the corrosion zone by staining and subsequent inspection, wherein the staining comprises charging a solution of methylene blue is into the empty glass packaging and allowing the charged empty glass packaging to stand at room temperature.

8. The rapid test method as claimed in claim 7, wherein the charged empty glass packaging charged to stand at room temperature for several minutes to several hours.

9. The rapid test method as claimed in claim 7, wherein the subsequent inspection comprises visual inspection.

10. The rapid test method as claimed in claim 1, wherein the further step comprises dissolving glass components in ultrapure water and quantifying the dissolved glass components, wherein the step of dissolving glass components in ultrapure water comprises charging the empty glass packaging with the ultrapure water and storing the charged empty glass packaging at an elevated temperature, and wherein the step of quantifying the dissolved glass components comprises determining an amount or concentration of the glass components dissolved in the ultrapure water.

11. The rapid test method as claimed in claim 10, wherein the elevated temperature is above 50 degrees Celsius.

12. The rapid test method as claimed in claim 1, wherein the further step comprises dissolving glass components in ultrapure water and quantifying the dissolved glass components, wherein the step of dissolving glass components in ultrapure water comprises charging the empty glass packaging with ultrapure water and autoclaving the charged empty glass packaging at a temperature between 80 degrees Celsius and 150 degrees Celsius for a period from 0.5 to 8 hours, and wherein the step of quantifying the dissolved glass components comprises subsequently determining the amount or concentration of the glass components dissolved in the ultrapure water.

13. The rapid test method as claimed in claim 12, wherein the period is 2 hours.

14. The rapid test method as claimed in claim 12, wherein the amount or concentration of the glass components dissolved in the ultrapure water is determined using a method selected from the group consisting of ICP-OES, ICP-MS, and FAAS.

15. The rapid test method as claimed in claim 1, wherein the empty glass packaging is selected from the group consisting of bottles, vials, phials, ampoules, cartridges, capsules, and syringes.

16. The rapid test method as claimed in claim 1, further comprising cleaning the empty glass packaging means before and/or after exposing the empty glass packaging to the atmosphere of steam.

17. The rapid test method as claimed in claim 16, wherein the cleaning comprises multiple rinsing of the empty glass packaging by charging with water, emptying the water from the empty glass packaging, and blowing dry the empty glass packaging means with inert gas.

18. The rapid test method as claimed in claim 16, wherein the water comprises mains water, demineralized water or ultrapure water.

19. The rapid test method as claimed in claim 16, wherein a final rinsing operation comprising rinsing with demineralized water or ultrapure water.

20. The rapid test method as claimed in claim 16, wherein the inert gas is nitrogen.

21. The rapid test method as claimed in claim 16, wherein the water for rinsing is at room temperature.

22. The rapid test method as claimed in claim 16, wherein the water for rinsing is preheated to a temperature above room temperature.

23. The rapid test method as claimed in claim 22, wherein the water for rinsing is preheated to above 50 degrees Celsius.

24. The rapid test method as claimed in claim 1, wherein the further step comprises dissolving glass components in ultrapure water and quantifying the dissolved glass components, and wherein, before the dissolving step, the empty glass packaging is not rinsed with water.

* * * * *